(12) United States Patent
Gillet et al.

(10) Patent No.: US 11,339,123 B2
(45) Date of Patent: May 24, 2022

(54) ALKOXYLATED SECONDARY ALCOHOL SULFATES

(71) Applicant: Arkema France, Colombes (FR)

(72) Inventors: Jean-Philippe Gillet, Brignais (FR); Juan Antonio Gonzalez Leon, Lyons (FR); Carl Bouret, Chateauroux (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/761,379

(22) PCT Filed: Nov. 8, 2018

(86) PCT No.: PCT/FR2018/052763
§ 371 (c)(1),
(2) Date: May 4, 2020

(87) PCT Pub. No.: WO2019/092368
PCT Pub. Date: May 16, 2019

(65) Prior Publication Data
US 2020/0361862 A1    Nov. 19, 2020

(30) Foreign Application Priority Data
Nov. 10, 2017 (FR) ...................................... 1760597

(51) Int. Cl.
    *C07C 305/10*     (2006.01)
    *C09K 23/00*     (2022.01)

(52) U.S. Cl.
    CPC ............ *C07C 305/10* (2013.01); *C09K 23/00* (2022.01)

(58) Field of Classification Search
    CPC .................................................. C07C 305/10
    See application file for complete search history.

(56) References Cited

U.S. PATENT DOCUMENTS

| | | | |
|---|---|---|---|
| 3,346,667 | A | 10/1967 | Firth |
| 3,395,170 | A | 7/1968 | Walts et al. |
| 3,803,238 | A | 4/1974 | Struve et al. |
| 5,611,991 | A | 3/1997 | Naraghi |
| 6,429,342 | B1 | 8/2002 | Clement et al. |
| 6,830,612 | B1 | 12/2004 | Yatake et al. |
| 6,977,236 | B2 | 12/2005 | Eleveld et al. |
| 2008/0045415 | A1 | 2/2008 | Baur et al. |
| 2010/0122622 | A1 | 5/2010 | Takegawa |

FOREIGN PATENT DOCUMENTS

| | | |
|---|---|---|
| DE | 4436066 A1 | 4/1996 |
| FR | 2138763 A1 | 1/1973 |
| GB | 758061 | 9/1956 |
| JP | 47035123 A | 11/1972 |
| JP | 497212 B1 | 2/1974 |
| JP | 60119265 A | 6/1985 |
| JP | 01290604 A | 11/1989 |
| JP | 0920874 A | 1/1997 |
| JP | 2000327974 A | 11/2000 |
| JP | 2001064551 A | 3/2001 |
| JP | 2011105874 A | 6/2011 |
| JP | 2016044299 A | 4/2016 |
| JP | 2017048315 A | 3/2017 |
| WO | 0104183 A1 | 1/2001 |
| WO | 2009000852 A1 | 12/2008 |
| WO | 2009039018 A1 | 3/2009 |
| WO | 2012005897 A1 | 1/2012 |
| WO | 2012071149 A2 | 5/2012 |

OTHER PUBLICATIONS

Kataoka et al (1990) : STN International CAPLUS database, (Columbus, Ohio), Accession No. 1990: 493313.*
Shirai et al (2011): STN International CAPLUS database, (Columbus, Ohio), Accession No. 2011: 684667.*
Kadonome et al (2014) : STN International CAPLUS database, (Columbus, Ohio), Accession No. 2014: 1980740.*
Sugimoto et al (1975) : STN International CAPLUS database, (Columbus, Ohio), Accession No. 1975: 52646.*
Domingo, X., "Alcohol and Alcohol Ether Sulfates," 1996, vol. 56, Chapter 5, pp. 223-312, Anionic Surfactants.
Dekker, M., "Phosphorus-Containing Anionic Surfactants: Organic Chemistry", vol. 56, Marcel Dekker, 1996, pp. 552-564.
Bakker, "Sulfonates and sulfates of sec-alkyl ethyl ether: detergents prepared by the addition of substituted alcohols to 1-alkenes", Chimie, Physique Et Applications Pratiques Des Agents De Sur Fact, Sep. 9, 1968, pp. 157-165.
Encyclopedia of Chemical Technology, 4th edition, Kirk Othmer, 1997, vol. 23, pp. 146-175.
Encyclopedia of Chemical Technology, 4th edition, Kirk-Othmer, 1997, vol. 23, pp. 504-505.
Johnson et al., "Topical mosquito repellents VII; Alkyl triethylene glycol monoethers", Journal of Pharmaceutical Sciences, Mar. 31, 1975, 64(4):693-695.

(Continued)

*Primary Examiner* — Golam M Shameem
(74) *Attorney, Agent, or Firm* — RatnerPrestia

(57) ABSTRACT

The invention relates to the compounds of formula (I), $$\begin{array}{c} R_1 \\ \phantom{R}\diagdown \\ \phantom{R_1R_2}\diagup \\ R_2 \end{array} \!\!\!\! O\!\!-\!\!\left[\!A\!\right]_{\!n}\!\!-\!\!\overset{\displaystyle O}{\underset{\displaystyle O}{\overset{\|}{\underset{\|}{S}}}}\!\!-\!\!OH \quad (\mathrm{I})$$

in which $R_1$ and $R_2$ represent a linear, branched or cyclic, saturated or unsaturated hydrocarbon group, comprising 1 to 6 carbon atoms, wherein the sum of the carbon atoms of the groups $R_1$ and $R_2$ is from 2 to 7; A represents a chain of one or a plurality of units of ethylene oxide, propylene oxide, butylene oxide and mixtures thereof; and n is an integer between 1 and 100 inclusive. The invention also relates to mineral or organic salts thereof; the use of the compounds of formula (I) and/or of one of the salts thereof as a surfactant, a wetting agent, a detergent, an emulsifying agent, a dispersant, a corrosion inhibitor, and the like; and to compositions comprising at least one compound of formula (I) and/or of one of the salts thereof.

6 Claims, No Drawings

(56) References Cited

OTHER PUBLICATIONS

Stockburger et al., "The reactions of alkylene oxides with various butyl and other alcohols" JAOC, vol. 40, No. 10, Oct. 1, 1963, pp. 590-594.
Ullmann's Encyclopedia of Industrial Chemistry, 5th edition. Elvers, B., Hawkins. S., Schulz, G., 1994, vol. A 19, pp. 562-564.
Ullmann's Encyclopedia of Industrial Chemistry, 5th edition, Elvers, 15 B., Hawkins, S., Schulz, G., 1994, vol. A 25, pp. 778-783.
Wang et al., "Synthesis and properties of two surfactants containing polyoxypropylene block and short branched alkyl chain", Journal of Molecular Liquids, Elsevier, Amsterdam, NL, vol. 220, Apr. 26, 2016 (Apr. 26, 2016), pp. 101-107.
International Search Report and Written Opinion for International Application No. PCT/EP2018/052761, dated Jan. 25, 2019, 9 pages.
International Search Report and Written Opinion for International Application No. PCT/EP2018/052762, dated Feb. 12, 2019, 7 pages.
International Search Report and Written Opinion for International Application No. PCT/EP2018/052763, dated Apr. 24, 2019, 10 pages.
Non Final Office Action for U.S. Appl. No. 16/760,564, dated Oct. 29, 2020, 13 pages.
Non-Final Office Action for U.S. Appl. No. 16/760,564, dated May 12, 2021, 8 pages.
SCI Finder CAS RN771417-41-5, 2021, 2 pages.
Japanese Notice of Rejection for Japanese Application No. 2020-525877, dated May 18, 2021, with English translation, 4 pages.
Case Registry No. 771417-41-5, dated Oct. 28, 2004, 5 pages.
Case Registry No. 53640-13-4, dated Nov. 16, 1984, 5 pages.
Korean Notice of Grounds for Rejection for Korean Application No. 10-2020-7013149, dated Sep. 3, 2021, 11 pages.
Non Final Office Action for U.S. Appl. No. 16/761,652, dated Oct. 27, 2021, 41 pages.

\* cited by examiner

ALKOXYLATED SECONDARY ALCOHOL SULFATES

CROSS-REFERENCE TO RELATED APPLICATIONS

This is the national phase of International Application No. PCT/FR2018/052763, filed 8 Nov. 2018, which claims priority to French Application No. 1760597, filed 10 Nov. 2017. The disclosure of each of these applications is incorporated herein by reference in its entirety for all purposes.

The present invention relates to the general field of alkoxylated secondary alcohols which have been subjected to a sulfatation reaction.

The sulfatation of organic alcohols is a well-known route for obtaining organic alcohol sulfates. Fatty alcohol sulfates are known as surfactants in various applications. Specifically, they have a certain number of intrinsic properties in comparison with other cationic and anionic surfactants.

The main intermediary for the synthesis of organic alcohol sulfates is the organic alcohol itself. Various properties for an alcohol sulfate may be obtained, depending on the organic alcohol chosen as starting material.

The organic alcohols used for synthesizing these sulfates may be of very different nature, for example: linear or branched, of small or large molar mass, monofunctional or polyfunctional, inter alia.

They may also be organic alcohols which have undergone an alkoxylation step, in which one or more units of an alkyl oxide, for example ethylene oxide, propylene oxide or butylene oxide, have been incorporated into said organic alcohol.

The synthesis of organic alcohol sulfates is of real industrial interest, most particularly when this synthesis is simple and inexpensive to perform, notably starting with available starting materials that are readily modifiable to obtain various properties.

In addition, at a time when the environmental challenges are truly high, it is entirely interesting to envisage using a biobased or biodegradable reagent having a good ecotoxicological profile.

Secondary alcohol alkoxylates are a family of compounds which offer a wide range of properties. Indeed, the applications are manifold. They may notably be used as solvents, as hydrotropes or even as nonionic surfactants. They may also act as starting material to other compounds, such as etheramines or anionic surfactants obtained by phosphatation or sulfatation. Thus, secondary alcohol alkoxylates constitute a class of compounds that are of major industrial interest for many players.

Secondary alcohol alkoxylates are conventionally synthesized by means of basic catalysis, for example using potassium hydroxide. Another type of catalyst may also be used: the catalyst of dimetallic cyanide type, commonly known as a DMC catalyst. Various documents mention the alkoxylation of various compounds, including alcohols, by basic catalysis and/or by DMC catalysis.

Thus, a secondary alcohol sulfate is sought, said alcohol being short-chained and alkoxylated, the alkoxylation of which is performed via a simple process that allows low-cost industrial and commercial development. It would also be advantageous to develop a process for preparing these sulfates using alkoxylated secondary alcohols, the starting compound of which is a biobased and biodegradable reagent.

One object of the present invention is to propose a solution for resolving the problems mentioned above.

One subject of the present invention is the compounds of formula (I) below:

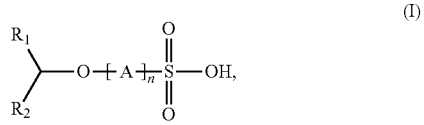

in which:
the groups $R_1$ and $R_2$, which may be identical or different, represent, independently of each other, a linear, branched or cyclic, saturated or unsaturated hydrocarbon-based group, comprising from 1 to 6 carbon atoms, it being understood that the sum of the carbon atoms of the groups $R_1$ and $R_2$ ranges from 2 to 7, $R_1$ and $R_2$ possibly forming, together with the carbon atom that bears them, a 6-, 7- or 8-membered ring, A represents a sequence of one or more units chosen from ethylene oxide, propylene oxide and butylene oxide units, and mixtures thereof, and n is an integer between, limits inclusive, 1 and 100, preferably between 2 and 100, more preferably between 3 and 100, more particularly between 5 and 100 and very preferably between 10 and 100.

A subject of the present invention is also the salts of the compounds of formula (I) above with one or more cationic groups bearing at least one cation chosen from an ammonium cation, a metal cation, a nitrogen cation, a boron cation and a phosphorus cation.

Examples of these salts may be described by formula (II) below:

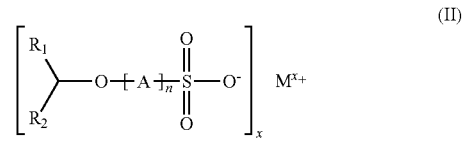

in which:
$M^{x+}$ represents a cationic group bearing at least one cation chosen from an ammonium cation, a metal cation, a nitrogen cation, a boron cation and a phosphorus cation, x is an integer ranging from 1 to 7, and $R_1$, $R_2$, A and n are as defined previously.

A subject of the present invention is also the use of at least one compound of formula (I) and of at least one compound of formula (II). In the rest of the present description, and unless otherwise mentioned, the term "compound of formula (I)" denotes at least one compound of formula (I) or at least one salt thereof of formula (II) or a mixture of at least one compound of formula (I) with at least one salt thereof of formula (II).

Another subject of the invention is the use of the compound of formula (I) according to the invention, as surfactant, low-foaming surfactant, wetting agent, foaming agent, hydrotrope, detergent, solvent, reactive solvent, coalescer, compatibilizer, emulsifying agent, dispersant, chemical intermediary, corrosion inhibitor, demulcent, plasticizer, sequestrant, mineral deposition inhibitor, ionic liquid, stabilizer, lubricant, bitumen additive, deinking additive, oil gellant, ore flotation collector, processing aid in the manufacture of plastics, antistatic agent, fertilizer coating additive, for plant protection, for treating textiles and for enhanced oil recovery, for the production of electrodes and electrolytes for batteries.

Other advantages and features of the invention will emerge more clearly apparent on examining the detailed description. It is specified that the expression "from . . . to . . . " used in the present description should be understood as including each of the limits mentioned.

For the purposes of the present invention, the term "ethylene oxide unit" refers to the unit derived from ethylene oxide after opening of the oxirane ring. Similarly, the term "propylene oxide unit" refers to the unit derived from propylene oxide after opening of the oxirane ring. Similarly also, the term "butylene oxide unit" refers to the unit derived from butylene oxide after opening of the oxirane ring.

The compound according to the invention is a compound of formula (I) as mentioned above or a salt thereof of formula (II) as mentioned above.

In other words, the groups $R_1$ and $R_2$, with the carbon atom to which they are attached, denote a secondary radical comprising from 3 to 8 carbon atoms, preferably from 6 to 8 carbon atoms.

Preferably, the radicals $R_1$ and $R_2$, which may be identical or different, represent, independently of each other, methyl, ethyl, n-propyl, isopropyl, n-butyl, sec-butyl, tert-butyl, pentyl or hexyl radicals.

Preferably, the radical formed by $R_1$, $R_2$ and the carbon atom to which $R_1$ and $R_2$ are attached is chosen from the 2-octyl radical and the 4-methyl-2-pentyl radical. More particularly, the radical formed by $R_1$, $R_2$ and the carbon atom to which $R_1$ and $R_2$ are attached is the 2-octyl radical.

Advantageously, n is between, limits inclusive, 1 and 75, preferably between 2 and 75, more preferably between 3 and 75, more particularly between 5 and 75 and very preferably between 10 and 75.

Advantageously, n is between, limits inclusive, 1 and 50, preferably between 2 and 50, more preferably between 3 and 50, more particularly between 5 and 50 and very preferably between 10 and 50.

Advantageously, n is between, limits inclusive, 1 and 30, preferably between 2 and 30, more preferably between 3 and 30, more particularly between 5 and 30 and very preferably between 10 and 30.

Preferably, n ranges from 2 to 30.

As indicated previously, A represents a sequence of one or more units chosen from ethylene oxide, propylene oxide and butylene oxide units, and mixtures thereof. According to a particular embodiment, when the compound of formula (I) includes a mixture of said different units, they may be distributed randomly, alternately or in blocks.

According to a preferred embodiment, A represents a sequence of at least one ethylene oxide unit and of at least one propylene oxide unit, distributed alternately, randomly or in blocks.

According to yet another preferred embodiment, A represents a sequence of at least one ethylene oxide unit and of at least one butylene oxide unit, distributed alternately, randomly or in blocks.

According to yet another preferred embodiment, A represents a sequence of at least one propylene oxide unit and of at least one butylene oxide unit, distributed alternately, randomly or in blocks.

According to a preferred embodiment of the invention, the group formed by $R_1$, $R_2$ and the carbon atom to which $R_1$ and $R_2$ are attached represents the 2-octyl radical, n ranges from 3 to 15, and A represents a sequence of one or more units chosen from ethylene oxide, propylene oxide and butylene oxide units, and mixtures thereof.

The invention also relates to mixtures of the mixtures of secondary alcohol sulfates according to formula (I) as defined above.

A subject of the invention is also the salts of the compounds of formula (I) as defined above.

More precisely, a subject of the invention is the compound of formula (I) in the form of a salt with an alkali metal cation, and alkaline-earth metal cation, a metal cation or with an organic compound, including organic bases.

As indicated previously, these salts may be addition salts of a compound of formula (I) with an organic or mineral base.

These salts may be salts of organic amines, said amines possibly containing one or two or several amine groups. The amines that may be used for salifying the compounds of formula (I) as defined previously are preferably chosen, in a nonlimiting manner, from alkylamines, cycloalkylamines, aromatic amines and alkanolamines, said amines possibly being primary, secondary or tertiary, and also possibly being alkoxylated.

The compounds of formula (I) may also be salts of heterocyclic amines or of urea. The salts of the compounds of formula (I) with the ammonium cation ($NH_4^+$) also form part of the invention.

These salts may be inorganic salts. Advantageously, they are the salts of the compounds of formula (I) with the elements from column 1 of the Periodic Table of the Elements (alkali metals), for instance lithium, sodium, potassium, rubidium and cesium.

According to another advantageous embodiment of the present invention, the salts of the compounds of formula (I) with the elements from column 2 of the Periodic Table of the Elements (alkali metals), for instance magnesium and calcium.

According to yet another advantageous embodiment of the present invention, the salts of the compounds of formula (I) are the salts with the elements from columns 3 to 13 of the Periodic Table of the Elements (transition metals), for example vanadium, manganese, cobalt, zirconium, yttrium, iron, cadmium, aluminum and zinc.

Still according to another advantageous embodiment of the present invention, the salts of the compounds of formula (I) are those with rare earths (lanthanides and actinides), for instance lanthanum, cerium, thorium, uranium and plutonium.

The compound of formula (I) according to the present invention may be advantageously obtained by sulfatation of an alkoxylated secondary alcohol, according to the methods that are well known to those skilled in the art. For example, the sulfatation consists in reacting the secondary alcohol with a sulfate-based compound chosen from sulfur trioxide, sulfuric acid, oleum, sulfur trioxide, sulfur trioxide complexes, sulfamic acid and chlorosulfonic acid, inter alia.

As indicated previously, the synthesis of these sulfates and the features of their processes for preparing same are known to those skilled in the art and are described, for example, by X. Domingo in *Anionic Surfactants*, volume 5, H. W. Stache, (1996), pages 224-279, *Encyclopedia of Chemical Technology*, Kirk Othmer, 4$^{th}$ edition, (1997), volume 23, pages 146-175; *Ullmann's Encyclopedia of Industrial Chemistry*, 5$^{th}$ edition, Elvers, B., Hawkins, S., Schulz, G., (1994), volume A25, pages 778-783.

Preferably, the secondary alcohol used for synthesizing the compound of formula (I) is chosen from 2-octanol and methylisobutylcarbinol; preferably, the secondary alcohol is 2-octanol.

This alcohol is of particular interest in several respects. Specifically, it is a biobased, biodegradable product and has a good ecotoxicological profile. In addition, the boiling point of 2-octanol is high and its cost price is entirely reasonable.

According to a preferred embodiment, the alkoxylation of the secondary alcohol used for synthesizing the compound of formula (I) is obtained by means of a catalyst of dimetallic cyanide type, known as a DMC catalyst. Preferably, the catalyst of dimetallic cyanide type may be of any nature known to a person skilled in the art. This catalyst is notably described in U.S. Pat. Nos. 6,429,342, 6,977,236 and PL 398 518. More particularly, the catalyst used is zinc hexacyanocobaltate, which is sold, for example, by the company Bayer under the name Arcol® or by the company Mexeo under the name MEO-DMC®.

Another subject of the invention is the use of the compound of formula (I) according to the invention defined previously, and/or a salt thereof, alone or as a mixture, as surfactant, low-foaming surfactant, wetting agent, foaming agent, hydrotrope, detergent, solvent, reactive solvent, coalescer, compatibilizer, emulsifying agent, dispersant, chemical intermediary, corrosion inhibitor, demulcent, plasticizer, sequestrant, mineral deposition inhibitor, ionic liquid, stabilizer, lubricant, bitumen additive, deinking additive, oil gellant, ore flotation collector, processing aid in the manufacture of plastics, antistatic agent, fertilizer coating additive, for plant protection, for treating textiles and for enhanced oil recovery, for the production of electrodes and electrolytes for batteries, to mention but a few applications among the most common ones known for this type of compound.

According to yet another subject, the present invention relates to a composition comprising at least one compound of formula (I) as defined previously, and/or a salt thereof, alone or as a mixture, with one or more aqueous, organic or aqueous-organic solvents, for instance water, alcohols, glycols, polyols, mineral oils, plant oils, and the like, alone or as mixtures of two or more thereof, in all proportions.

The composition according to the invention may also contain one or more additives and fillers that are well known to those skilled in the art, for instance, in a nonlimiting manner, anionic, cationic, amphoteric or nonionic surfactants, rheology modifiers, demulcents, deposition-inhibiting agents, antifoams, dispersants, pH control agents, colorants, antioxidants, preserving agents, corrosion inhibitors, biocides, and other additives, for instance sulfur, boron, nitrogen or phosphate products, and the like. The nature and amount of the additives and fillers may vary within wide proportions depending on the nature of the intended application and may readily be adapted by a person skilled in the art.

The invention is now illustrated by the examples that follow, which are not in any way limiting.

EXAMPLES

The 2-octanol (CAS RN 123-96-6) used is the "refined" grade 2-octanol Oleris® (purity >99%), sold by Arkema France.

Example 1

Synthesis of Propoxylated 2-Octanol Sulfate

Step 1a: Propoxylation of 2-Octanol 591 g (4.54 mol) of 2-octanol dried to less than 200 ppm of water and 0.06 g (100 ppm) of catalyst DMC Arcol® are placed in a clean, dry 4 L autoclave. The reactor is closed and purged with nitrogen and the leaktightness under pressure is checked. The reactor is pressurized with nitrogen to 0.225 MPa at 27° C.

The reaction medium is brought to 90° C. with stirring, and the temperature is then increased to 120° C. At this temperature of 120° C., 40 g of propylene oxide are introduced. When initiation of the reaction is observed, the rest of the propylene oxide is introduced, i.e. 792 g (13.62 M) in total over a period of 60 minutes at a temperature of 140° C.-150° C. At the end of the addition, the temperature is maintained for 30 minutes and the residual propylene oxide is then removed by flushing (stripping) with nitrogen. The reactor is cooled to 60° C. and 1381 g of alkoxylated 2-octanol comprising 3 propylene oxide units (3 PO) are withdrawn.

Step 1b: Sulfatation of Propoxylated 2-Octanol

The 2-octanol propoxylated with 3 PO (304 g; 1 M) obtained in Step 1a above are placed in a stirred 500 cm³ reactor equipped with a stirrer, a solids-addition funnel and under an inert atmosphere of nitrogen. The system is brought to 110° C. with stirring and sparging with nitrogen. The water content, which must be below 2500 ppm, is checked by assaying. The temperature is then brought to 130° C. and the introduction of sulfamic acid (101.5 g; 1.05 M) is commenced. The rate of introduction is controlled to maintain a temperature of 130° C. The system is then left stirring for 1 hour at 130° C.

It is then cooled to 70° C. 0.05 M aqueous ammonia solution is then added dropwise so as to neutralize the excess sulfamic acid. The system is then emptied into a flask. 390 g of product are recovered.

The reaction is represented schematically below:

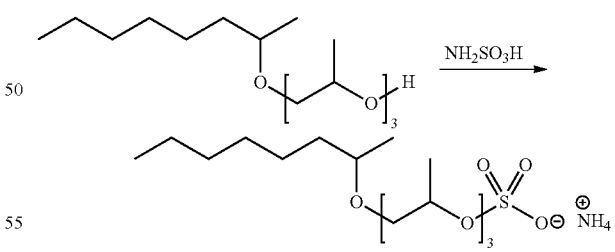

Example 2

Ethoxylated 2-Octanol Sulfate

Step 2a: Ethoxylation of 2-Octanol 619 g (4.76 M) of 2-octanol dried to less than 200 ppm of water and 0.06 g (100 ppm) of catalyst DMC Arcol® are placed in a clean, dry 4 L autoclave. The reactor is closed and purged with nitrogen and the leaktightness under pressure is checked. The reactor is pressurized with nitrogen to 0.269 MPa at 20° C.

The reaction medium is brought to 120° C. with stirring. At this temperature of 120° C., 40 g of ethylene oxide are introduced. When initiation of the reaction is observed, the rest of the ethylene oxide is introduced, i.e. 628 g (14.27 M) in total over 60 minutes at a temperature of 140° C.-150° C. At the end of the addition, the temperature is maintained for 30 minutes and the residual ethylene oxide is then stripped out with nitrogen. The reactor is cooled to 60° C. and 1240 g of alkoxylated 2-octanol comprising 3 ethylene oxide units are withdrawn. (OHN: 210 mg of KOH/g and coloration of 26 Hz).

Step 2b: Sulfatation of Ethoxylated 2-Octanol 262 g (1 M) of ethoxylated 2-octanol obtained in Step 2a are placed in a 500 cm³ reactor, under an inert atmosphere, and 116 g (1 M) of chlorosulfonic acid are then added dropwise with stirring. The addition of the chlorosulfonic acid is performed while controlling the temperature, which must not exceed 30° C. At the end of the addition, the temperature of the reactor is maintained at 30° C. for 20 minutes with stirring. The hydrochloric acid is removed continuously by sparging nitrogen into the reaction medium.

The reaction is monitored by means of the amount of hydrochloric acid produced. The reaction is considered to be complete when the values no longer change. 340 g of alkoxylated 2-octanol sulfate comprising 3 ethylene oxide units (3 EO) are recovered.

The reaction is represented schematically below:

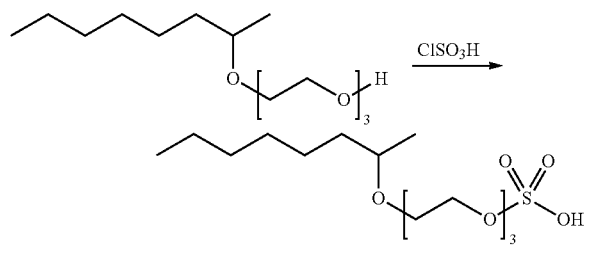

Example 3

Salification with Sodium Hydroxide 342 g (1 M) of ethoxylated 2-octanol sulfate obtained as described previously (example 4) are placed in a 1 L reactor. 80 g (2 M) of sodium hydroxide are then added with stirring. At the end of the addition, the temperature of the reactor is maintained at 60° C. for 15 minutes with stirring. The reactor is then cooled and the product is isolated.

About 380 g of the sodium salt of the alkoxylated 2-octanol sulfate comprising 3 ethylene oxide units are recovered.

Example 4

Salification with a Fatty Amine 342 g (1 M) of the ethoxylated 2-octanol sulfate obtained in example 2 as described previously are placed in a 1 L reactor. The reactor is heated to 80° C. and 259 g (1 M) of a fatty amine bearing a chain of about 18 carbon atoms, sold by Arkema France under the name Noram SH®, are then added with stirring while controlling the temperature, which must not exceed 80° C. At the end of the addition, the temperature of the reactor is maintained at 80° C. for 15 minutes with stirring. The reactor is then cooled and the synthesized product is recovered.

About 600 g of the fatty amine salt of the alkoxylated 2-octanol sulfate comprising 3 ethylene oxide units are thus recovered.

The invention claimed is:

1. A compound of formula (I) below:

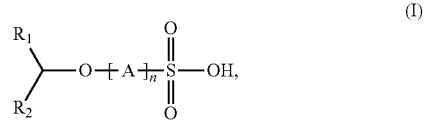

wherein:
$R_1$ and $R_2$, together with the carbon atom that bears $R_1$ and $R_2$ forms a 2-octyl radical;
A represents a sequence of one or more units chosen from ethylene oxide, propylene oxide and butylene oxide units, and mixtures thereof; and
n is an integer between, limits inclusive, 1 and 100.

2. The compound as claimed in claim 1, in the form of a salt with an alkali metal cation, and alkaline-earth metal cation, a metal cation or with an organic compound.

3. The compound as claimed in claim 1, wherein n is between, limits inclusive, 1 and 75.

4. The compound as claimed in claim 1, wherein n is between, limits inclusive, 1 and 50.

5. The compound as claimed in claim 1, wherein n ranges from 3 to 15.

6. A salt of the compound as claimed in claim 1, corresponding to formula (II) below:

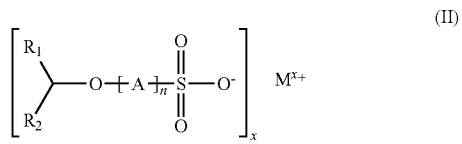

wherein:
$M^{x+}$ represents a cationic group bearing at least one cation chosen from an ammonium cation, a metal cation, a nitrogen cation, a boron cation and a phosphorus cation, and
x is an integer ranging from 1 to 7.

* * * * *